United States Patent
Nirogi et al.

(10) Patent No.: US 11,253,514 B2
(45) Date of Patent: Feb. 22, 2022

(54) TRIPLE COMBINATION OF PURE 5-HT$_6$ RECEPTOR ANTAGONISTS, ACETYLCHOLINESTERASE INHIBITORS AND NMDA RECEPTOR ANTAGONIST

(71) Applicant: SUVEN LIFE SCIENCES LIMITED, Telangana (IN)

(72) Inventors: Ramakrishna Nirogi, Telangana (IN); Anil Karbhari Shinde, Telangana (IN); Pradeep Jayarajan, Telangana (IN); Gopinadh Bhyrapuneni, Telangana (IN); Ramasastri Kambhampati, Telangana (IN); Venkateswarlu Jasti, Telangana (IN)

(73) Assignee: Suven Life Sciences Limited, Hyderabad (IN)

( * ) Notice: Subject to any disclaimer, the term of this patent is extended or adjusted under 35 U.S.C. 154(b) by 286 days.

(21) Appl. No.: 16/097,752

(22) PCT Filed: Aug. 3, 2016

(86) PCT No.: PCT/IB2016/054672
§ 371 (c)(1),
(2) Date: Oct. 30, 2018

(87) PCT Pub. No.: WO2017/199070
PCT Pub. Date: Nov. 23, 2017

(65) Prior Publication Data
US 2019/0160055 A1 May 30, 2019

(30) Foreign Application Priority Data
May 18, 2016 (IN) .............................. 201641017204

(51) Int. Cl.
*A61K 31/496* (2006.01)
*A61K 31/13* (2006.01)
*A61K 31/445* (2006.01)
*A61P 25/28* (2006.01)

(52) U.S. Cl.
CPC ............ *A61K 31/496* (2013.01); *A61K 31/13* (2013.01); *A61K 31/445* (2013.01); *A61P 25/28* (2018.01)

(58) Field of Classification Search
CPC .................................................. A61K 31/496
See application file for complete search history.

(56) References Cited

FOREIGN PATENT DOCUMENTS

| WO | 03/101458 | 12/2003 |
|----|-----------|---------|
| WO | 2004/048330 | 6/2004 |
| WO | 2011/083487 | 7/2011 |
| WO | 2015/083179 | 6/2015 |
| WO | 2015/158313 | 10/2015 |

OTHER PUBLICATIONS

Jayarajan et al., "5-HT6 Antagonist SUVN-502 Potentiates the Procognitive and Neurochemical Effects of Donepezil and Memantine" Alzheimer's & Dementia: The Journal of the Alzheimer's Association 11(7):P472 (Jul. 1, 2015) Poster Presentation P1-302. XP029353767.
Fan and Chiu, "Combotherapy and current concepts as well as future strategies for the treatment of Alzheimer's disease" Neuropsychiatric Disease and Treatment 10:439-451 (2014).
Wicke et al., "Investigational drugs targeting 5-HT6 receptors for the treatment of Alzheimer's disease" Expert Op. Investigational Drugs 24(12):1515-1528 (2015).
Nirogi et al., "SUVN-502: A Potent and Selective 5-HT6 Antagonist, Potential Drug for the Treatment of Alzheimer's Disease" Alzheimer's & Dementia: The Journal of the Alzheimer's Association p. S659 (Jul. 1, 2011). Poster Presentations P3-451. XP55335504.
European Patent Office, "International Search Report" and "Written Opinion" dated Feb. 1, 2017 in PCT Application No. PCT/IB2016/054672.
European Patent Office, "International Preliminary Report on Patentability" completed Aug. 7, 2018, and Response to Written Opinion dated Jun. 6, 2018, in PCT Application No. PCT/IB2016/054672.
Parsons et al., "Memantine and Cholinesterase Inhibitors: Complementary Mechanisms in the Treatment of Alzheimer's Disease" Neurotox. Res. 24:358-369 (2013).

*Primary Examiner* — Yong S. Chong
(74) *Attorney, Agent, or Firm* — IpHorgan Ltd.

(57) ABSTRACT

The present invention relates to a combination of pure 5-HT6 receptor antagonist, acetylcholinesterase inhibitor and NMDA receptor antagonist. Also, the present invention provides pure 5-HT6 receptor (5-HT6R) antagonists, or the pharmaceutically acceptable salt(s) thereof in combination with or as adjunct to acetylcholinesterase inhibitor and N-Methyl-D-aspartate (NMDA) receptor antagonist and their use in the treatment of cognitive disorders. The invention further provides the pharmaceutical composition containing the said combination.

16 Claims, 6 Drawing Sheets

Figure 1a

Data represents Mean ± SEM of discriminative index. *$p<0.05$ Vs vehicle (Kruskal-Wallis followed by Dunn's Multiple Comparison Test) N=11-12

Figure 1b

Data represents Mean ± SEM of discriminative index. ***$p<0.001$ Vs vehicle (Kruskal-Wallis followed by Dunn's Multiple Comparison Test) N=11-14

Figure 1c

Data represents Mean ± SEM of discriminative index. *$p<0.05$ Vs vehicle (Kruskal-Wallis followed by Dunn's Multiple Comparison Test) N=17-21

(a) Percent change from mean basal levels expressed as Mean ± SEM. $p<0.01$, *$p<0.001$ Vs donepezil + memantine combination (Bonferroni post test). (b) Cumulative changes in acetylcholine levels expressed as mean area under the curve (AUC) ± S.E.M. **$p<0.01$ (Dunnett's Multiple Comparison Test).

(a) Percent change from mean basal levels expressed as Mean ± SEM. *$p<0.05$, $p<0.01$, *$p<0.001$ Vs donepezil + memantine combination (Bonferroni post test). (b) Cumulative changes in acetylcholine levels expressed as mean area under the curve (AUC) ± S.E.M. *$p<0.05$ (Dunnett's Multiple Comparison Test).

(a) Percent change from mean basal levels expressed as Mean ± SEM. $*p<0.05$, $**p<0.01$, Vs donepezil + memantine combination (Bonferroni post test). (b) Cumulative changes in acetylcholine levels expressed as mean area under the curve (AUC) ± S.E.M. $*p<0.05$ (Dunnett's Multiple Comparison Test).

(a) Data expressed as Mean ± SEM. $*p<0.05$, $**p<0.01$ Vs donepezil and memantine combination (Bonferroni post test) (b) Area under the curve value ± SEM. $*p<0.05$ Vs donepezil + memantine combination (Dunnett's post test)

TRIPLE COMBINATION OF PURE 5-HT$_6$ RECEPTOR ANTAGONISTS, ACETYLCHOLINESTERASE INHIBITORS AND NMDA RECEPTOR ANTAGONIST

CROSS REFERENCE TO RELATED APPLICATIONS

This application is a national stage completion application of PCT Application No. PCT/IB2016/054672, filed Aug. 3, 2016, and claims the benefit of India Application No. 201641017204, filed May 18, 2016. Each of these applications is incorporated by reference herein in its entirety.

FIELD OF THE INVENTION

The present invention relates to pure 5-HT$_6$ receptor (5-HT$_6$R) antagonists or the pharmaceutically acceptable salt(s) thereof in combination with or as adjunct to acetylcholinesterase inhibitors and N-Methyl-D-aspartate (NMDA) receptor antagonist. The present invention further relates to the use of the combination and the pharmaceutical composition containing the said combination in the treatment of cognitive disorders.

BACKGROUND OF INVENTION

Alzheimer's disease (AD) is the most common cause of dementia worldwide. The exponential rise in the number of cases of AD in the past and the future projection over the next few decades is anticipated to result in great pressure on the social and health-care systems of developed and developing economies alike. AD also imposes tremendous emotional and financial burden to the patient's family and community.

The current list of approved cognitive enhancing drugs for AD is not long and historically been focused on acetylcholinesterase inhibitors (donepezil, rivastigmine and galantamine). These drugs act by inhibiting the hydrolysis of acetylcholine (ACh) into acetate and choline by targeting acetylcholinesterase (AChE) enzyme. Increasing the ACh levels in the synapse can stimulate cholinergic receptors and promote memory function. Although acetylcholinesterase inhibitors (AChEIs) can temporarily delay the progression of cognitive decline in AD, their effects are modest. ACh being present both in the central and peripheral nervous system, AChEIs produce several undesirable side effects such as gastrointestinal disturbances, bradycardia and excessive salivation that are associated with an action on peripheral muscarinic cholinergic receptors (*Expert Opinion on Drug Safety*, 3, 2004, 425-440). The limitation of AChEI class of drugs is that they are poorly tolerated, their efficacy is not sustained and they require constant dose-titration as the disease progresses (*Cochrane Database Systematic Reviews*, 2006, CD005593) which lead to significant patient noncompliance. The incidence and the severity of these side effects increase with the dose amount and in general more pronounced at the initiation of the treatment or after dose increase. Hence there is an unmet need of alternate therapy for treating cognition disorders.

5-Hydroxytryptamine 6 receptor (5-HT$_6$R), a member of GPCR family is exclusively expressed in the brain, particularly in areas associated with cognition, such as hippocampus and frontal cortex (*Molecular Pharmacology*, 1993, 43, 320-327). Activation of 5-HT$_6$R usually represses cholinergic function (*British Journal of Pharmacology*, 1999, 126, 1537-1542), whereas blockade of the receptor improves the cognitive functions. Thus, 5-HT$_6$R may be a viable target for pharmacologic intervention to improve the cognitive function of patients with AD. As 5-HT$_6$R is exclusively located centrally, it is believed that 5-HT$_6$R antagonists would have limited peripheral side effects, including the ones which are commonly associated with cholinesterase inhibitors. Antagonism of this receptor by several investigational compounds has been shown to improve learning and memory in animal models (*CNS & Neurological Disorders—Drug Targets*, 2004, 3, 59-79).

Since blocking 5-HT$_6$R modulates cholinergic activity, one might expect 5-HT$_6$R antagonists to complement and/or augment cognitive function through this therapeutic mechanism. This may in turn help to reduce the side effects with better patient compliance and thus can be administered over a longer period.

The glutamatergic system is also involved in learning and memory and is a target for treatment of Alzheimer's disease. Memantine is another approved treatment for Alzheimer's disease, which acts on the glutamatergic system by inhibiting NMDA receptor under conditions of excess stimulation. It may act to protect glutamate neurons from excessive glutamate stimulation, while increasing the signal to noise ratio. It is known that glutamate neurons have synaptic connections on cholinergic neurons in brain areas associated with learning and memory.

The 5-HT$_6$R antagonists have been shown to increase extracellular glutamate levels in addition to acetylcholine. It is thus possible that the cognitive effects of 5-HT$_6$R antagonists and other treatments for AD could be the result of interactions with both cholinergic and glutamatergic systems involved in learning and memory.

Since the cause and development of the dementia depend on the different mechanisms, it may be advantageous to use the combination of drugs working through different mechanisms for the treatment of AD. The current approved treatment for AD includes the combination of acetylcholinesterase inhibitor, donepezil and NMDA receptor antagonist, memantine. However, there remains the need for the new drugs/combination to treat the patients with AD.

The compounds of the present invention are pure 5-HT$_6$R antagonists with high affinity and very high selectivity over closely related serotonin receptor subtypes and improves learning and memory in animals. The 5-HT$_6$R antagonist compounds mentioned here are described in U.S. Pat. No. 7,875,605 which is incorporated by reference. The preparation of these compounds is given in the said patent.

As the treatment of AD is chronic in nature, there is a desperate unmet medical need for better and safer treatment options. A therapeutic strategy eagerly sought for AD patients is to target an improvement with an adjunct to existing therapies that would bring additional relief for patients, lower the burden on the caregiver and allow the patient to enjoy a better quality of life without the need for institutional care and/or hospitalization.

The instant invention provides pure 5-HT$_6$R antagonists or the pharmaceutically acceptable salt(s) thereof, which enhances the cognitive function of patients on treatment in combination with AChEIs and NMDA receptor antagonist. The present invention is based on the unusual finding that the combination of compounds with pure 5-HT$_6$R antagonistic activity, the compounds which act as AChEIs (for example donepezil) and the compounds which act as NMDA receptor antagonists (for example memantine), demonstrate synergistic effect in their pharmacological activity. Memantine acts by blocking the glutamatergic neurotransmissions in the brain. The 5-HT$_6$R antagonists have been shown to increase extracellular glutamate levels in addition to acetylcholine. Hence it is not anticipated that the combination of a pure 5-HT$_6$R antagonist+donepezil+memantine would result in synergistic procognitive effects. However surprisingly, the combination of pure 5-HT$_6$R antagonists+ AChEIs+NMDA receptor antagonist (triple combination) showed synergistic effects in animal models, and also increased the levels of acetylcholine, a neurotransmitter that plays a vital role in cognitive improvement. Based on these results one can infer that such combined administration and/or co-treatment of pure 5-HT$_6$R antagonists+AChEIs+ NMDA receptor antagonist, may result in beneficial effect to improve the therapeutic efficacy in humans. Further the pure 5-HT$_6$R antagonists or the pharmaceutically acceptable salt (s) thereof of the instant invention enhances the effect of the AChEIs and NMDA receptor antagonist in the treatment of cognitive disorders.

SUMMARY OF THE INVENTION

The object of the present invention is to provide an improved combination therapy for the treatment of cognitive disorders, such as Alzheimer's disease, schizophrenia, Parkinson's disease, lewy body dementia, vascular dementia or frontotemporal dementia.

In the first aspect, the present invention relates to a combination of pure 5-HT$_6$ receptor antagonist, acetylcholinesterase inhibitor and NMDA receptor antagonist.

In yet another aspect, the present invention relates to a combination of pure 5-HT$_6$ receptor antagonist, acetylcholinesterase inhibitor and NMDA receptor antagonist; wherein the pure 5-HT$_6$ receptor antagonist is selected from:
1-[(2-Bromophenyl)sulfonyl]-5-methoxy-3-[(4-methyl-1-piperazinyl) methyl]-1H-indole;
1-[(4-Fluorophenyl)sulfonyl]-5-methoxy-3-[(4-methyl-1-piperazinyl) methyl]-1H-indole; and
1-[(4-Isopropylphenyl)sulfonyl]-5-methoxy-3-[(4-methyl-1-piperazinyl) methyl]-1H-indole; or a pharmaceutically acceptable salt thereof.

In another aspect, the present invention relates to a combination of pure 5-HT$_6$ receptor antagonist, acetylcholinesterase inhibitor and NMDA receptor antagonist; wherein the pure 5-HT$_6$ receptor antagonist is 1-[(2-Bromophenyl)sulfonyl]-5-methoxy-3-[(4-methyl-1-piperazinyl) methyl]-1H-indole or a pharmaceutically acceptable salt thereof.

In another aspect, the present invention relates to a combination of pure 5-HT$_6$ receptor antagonist, acetylcholinesterase inhibitor and NMDA receptor antagonist; wherein the pure 5-HT$_6$ receptor antagonist is 1-[(4-Fluorophenyl)sulfonyl]-5-methoxy-3-[(4-methyl-1-piperazinyl) methyl]-1H-indole or a pharmaceutically acceptable salt thereof.

In another aspect, the present invention relates to a combination of pure 5-HT$_6$ receptor antagonist, acetylcholinesterase inhibitor and NMDA receptor antagonist; wherein the pure 5-HT$_6$ receptor antagonist is 1-[(4-Isopropylphenyl)sulfonyl]-5-methoxy-3-[(4-methyl-1-piperazinyl)methyl]-1H-indole or a pharmaceutically acceptable salt thereof.

In another aspect, the present invention relates to a combination of pure 5-HT$_6$ receptor antagonist, acetylcholinesterase inhibitor and NMDA receptor antagonist; wherein the acetylcholinesterase inhibitor is selected from donepezil, galantamine and rivastigmine or a pharmaceutically acceptable salt thereof.

In another aspect, the present invention relates to a combination of pure 5-HT$_6$ receptor antagonist, acetylcholinesterase inhibitor and NMDA receptor antagonist; wherein the NMDA receptor antagonist is memantine or a pharmaceutically acceptable salt thereof.

In yet another aspect the present invention relates to a combination of 1-[(2-Bromophenyl)sulfonyl]-5-methoxy-3-[(4-methyl-1-piperazinyl)methyl]-1H-indole, donepezil and memantine or a pharmaceutically acceptable salt thereof.

In yet another aspect, the present invention relates to the said combination for use in the treatment of cognitive disorders such as Alzheimer's disease, schizophrenia, Parkinson's disease, lewy body dementia, vascular dementia or frontotemporal dementia.

In yet another aspect, the present invention relates to a method of treatment of cognitive disorders such as Alzheimer's disease, schizophrenia, Parkinson's disease, lewy body dementia, vascular dementia or frontotemporal dementia comprising administering to a patient in need thereof a therapeutically effective amount of the said combination.

In yet another aspect, the present invention relates to pure 5-HT$_6$ receptor antagonist for use in the adjunct treatment of cognitive disorders such as Alzheimer's disease, schizophrenia, Parkinson's disease, lewy body dementia, vascular dementia or frontotemporal dementia in patients on treatment with acetylcholinesterase inhibitor and NMDA receptor antagonist.

In yet another aspect, the present invention relates to the compound, 1-[(2-Bromophenyl)sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia or frontotemporal dementia in patients on treatment with donepezil and memantine.

In yet another aspect, the present invention relates to the compound, 1-[(2-Bromophenyl)sulfonyl]-5-methoxy-3-[(4-methyl-1-piperazinyl)methyl]-1H-indole or a pharmaceutically acceptable salt thereof for use in combination with or adjunct to an acetylcholinesterase inhibitor and NMDA receptor antagonist for the treatment of cognitive disorders such as Alzheimer's disease, schizophrenia, Parkinson's disease, lewy body dementia, vascular dementia or frontotemporal dementia.

In another aspect, the present invention relates to a method for treatment of cognitive disorders comprising administering to a patient in need thereof a therapeutically effective amount of 1-[(2-Bromophenyl)sulfonyl]-5-methoxy-3-[(4-methyl-1-piperazinyl)methyl]-1H-indole or a pharmaceutically acceptable salt thereof in combination with or as an adjunct to donepezil or a pharmaceutically acceptable salt thereof and memantine or a pharmaceutically acceptable salt thereof.

In yet another aspect, the present invention relates to use of a combination of pure 5-HT$_6$ receptor antagonist, acetylcholinesterase inhibitor and NMDA receptor antagonist for the treatment of cognitive disorders such as Alzheimer's disease, schizophrenia, Parkinson's disease, lewy body dementia, vascular dementia or frontotemporal dementia.

In yet another aspect, the present invention relates to use of a combination of 1-[(2-Bromophenyl)sulfonyl]-5-methoxy-3-[(4-methyl-1-piperazinyl)methyl]-1H-indole, donepezil and memantine or a pharmaceutically acceptable salt thereof for the treatment of cognitive disorders such as Alzheimer's disease, schizophrenia, Parkinson's disease, lewy body dementia, vascular dementia or frontotemporal dementia.

In another aspect, the present invention relates to pharmaceutical composition comprising the 5-$HT_6$ receptor antagonist, acetylcholinesterase inhibitor and NMDA receptor antagonist and pharmaceutically acceptable excipients or combination thereof.

In another aspect, the present invention relates to pharmaceutical composition comprising 1-[(2-Bromophenyl) sulfonyl]-5-methoxy-3-[(4-methyl-1-piperazinyl)methyl]-1H-indole, donepezil and memantine or a pharmaceutically acceptable salt thereof and the pharmaceutically acceptable excipients or combination thereof.

In another aspect, the present invention relates to pharmaceutical composition comprising the 5-$HT_6$ receptor antagonist, acetylcholinesterase inhibitor and NMDA receptor antagonist or the pharmaceutically acceptable salt thereof along with the pharmaceutically acceptable excipients or combination thereof for use in the treatment of cognitive disorders such as Alzheimer's disease, schizophrenia, Parkinson's disease, lewy body dementia, vascular dementia or frontotemporal dementia.

BRIEF DESCRIPTION OF THE DIAGRAMS

DETAILED DESCRIPTION

Unless otherwise stated, the following terms used in the specification and claims have the meanings given below:

The term, "5-$HT_6$ receptor antagonist" as used herein refers to a ligand or drug that has affinity towards 5-$HT_6$ receptor, blocks or inhibits the function/binding of agonist at the 5-$HT_6$ receptor.

The term, "pure 5-$HT_6$ receptor antagonist" as used herein refers to 5-$HT_6$ receptor antagonist which has very high selectivity (>250 fold) over closely related serotonin subtypes like 5-$HT_{1A}$, 5-$HT_{1B}$, 5-$HT_{1D}$, 5-$HT_{2A}$, 5-$HT_{2C}$, 5-$HT_4$, 5-$HT_{5A}$ and 5-$HT_7$.

Examples of the pure 5-$HT_6$ receptor antagonists include, 1-[(2-Bromophenyl)sulfonyl]-5-methoxy-3-[(4-methyl-1-piperazinyl)methyl]-1H-indole;
1-[(4-Fluorophenyl)sulfonyl]-5-methoxy-3-[(4-methyl-1-piperazinyl)methyl]-1H-indole; and
1-[(4-Isopropylphenyl)sulfonyl]-5-methoxy-3-[(4-methyl-1-piperazinyl)methyl]-1H-indole;
or a pharmaceutically acceptable salt thereof.

Examples of pharmaceutically acceptable salt of the above identified compounds include but not limited to,
1-[(2-Bromophenyl)sulfonyl]-5-methoxy-3-[(4-methyl-1-piperazinyl)methyl]-1H-indole dimesylate monohydrate;
1-[(4-Fluorophenyl)sulfonyl]-5-methoxy-3-[(4-methyl-1-piperazinyl)methyl]-1H-indole dihydrochloride; and
1-[(4-Isopropylphenyl)sulfonyl]-5-methoxy-3-[(4-methyl-1-piperazinyl)methyl]-1H-indole dihydrochloride.

The term, "acetylcholinesterase inhibitor" as used herein is a chemical or drug that inhibits the acetylcholinesterase enzyme from breaking down acetylcholine, thereby increasing both the level and duration of action of the neurotransmitter acetylcholine. Examples of acetylcholinesterase inhibitor are donepezil, rivastigmine and galantamine. Preferably, the acetylcholinesterase inhibitor is donepezil and rivastigmine. More preferably the acetylcholinesterase inhibitor is donepezil.

Donepezil is a drug approved for treatment of mild, moderate and severe dementia of Alzheimer's disease. Donepezil is a reversible inhibitor of the enzyme acetylcholinesterase and sold under trade name Aricept® as hydrochloride salt.

Rivastigmine is a drug approved for treatment of mild, moderate and severe dementia of Alzheimer's disease. Rivastigmine is a reversible cholinesterase inhibitor and sold under trade name Exelon® and Exelon Patch® as tartrate salt.

Galantamine is a drug approved for treatment of mild, moderate and severe dementia of Alzheimer's disease. Galantamine, a reversible, competitive acetylcholinesterase inhibitor and sold under trade name Razadyne® as hydrobromide salt.

The term, "NMDA receptor antagonist" as used herein refers to class of compounds which act on glutamatergic system by inhibiting the NMDA receptor. Example of NMDA receptor antagonist is memantine. Memantine is a drug approved for treatment of moderate to severe dementia of the Alzheimer's disease. Memantine is NMDA receptor antagonist and sold under trade name Namenda® and Namenda XR® as hydrochloride salt.

The combination of memantine and donepezil is approved for the treatment of moderate to severe dementia of the Alzheimer's disease and sold under trade name Namzaric® as memantine hydrochloride salt and donepezil hydrochloride salt.

The phrase, "therapeutically effective amount" is defined as an amount of a compound of the present invention that (i) treats the particular disease, condition or disorder, (ii) eliminates one or more symptoms of the particular disease, condition or disorder and (iii) delays the onset of one or more symptoms of the particular disease, condition or disorder described herein.

The term, "pharmaceutically acceptable salt" as used herein refers to salts of the active compound and are prepared by reaction with the appropriate organic or inorganic acid or acid derivative, depending on the particular substituents found on the compounds described herein.

The term, "patient" as used herein refers to an animal. Preferably the term "patient" refers to mammal. The term mammal includes animals such as mice, rats, dogs, rabbits, pigs, monkeys, horses and human. More preferably the patient is human.

The term, "Alzheimer's disease" as used herein refers to a dementia that causes problems with memory, thinking and behavior. The Alzheimer's disease can be mild to severe.

The compound 1 as used herein is 1-[(2-Bromophenyl)sulfonyl]-5-methoxy-3-[(4-methyl-1-piperazinyl) methyl]-1H-indole dimesylate monohydrate which has the chemical structure, and the process for preparing this compound on a larger scale is described in WO2015083179A1.

The compound 2 as used herein is 1-[(4-Fluorophenyl)sulfonyl]-5-methoxy-3-[(4-methyl-1-piperazinyl)methyl]-1H-indole dihydrochloride which has the chemical structure, The compound 3 as used herein is 1-[(4-Isopropylphenyl)sulfonyl]-5-methoxy-3-[(4-methyl-1-piperazinyl)methyl]-1H-indole dihydrochloride which has the chemical structure, The term, "treatment' or 'treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a subject in need thereof.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Example of cognitive disorders includes but not limited to, Alzheimer's disease, schizophrenia, Parkinson's disease, lewy body dementia (LBD), vascular dementia or frontotemporal dementia (FTD). Preferably, the cognitive disorder is Alzheimer's disease.

The term, "adjunct" or "adjunctive treatment" as used herein refers to an additional treatment to a patient who has already received at least one other therapy for cognitive disorders. A drug used as adjunctive therapy is administered to a patient to make that primary treatment works better.

EMBODIMENTS

The present invention encompasses all the combinations described herein without limitation, however, preferred aspects and elements of the invention are discussed herein in the form of the following embodiments.

In one embodiment, the present invention relates to the combination of pure 5-$HT_6$ receptor antagonist, acetylcholinesterase inhibitor and NMDA receptor antagonist; wherein the pure 5-$HT_6$ receptor antagonist is 1-[(2-Bromophenyl)sulfonyl]-5-methoxy-3-[(4-methyl-1-piperazinyl)methyl]-1H-indole dimesylate monohydrate.

In another embodiment, the present invention relates to the combination of pure 5-$HT_6$ receptor antagonist, acetylcholinesterase inhibitor and NMDA receptor antagonist; wherein the pure 5-$HT_6$ receptor antagonist is 1-[(4-Fluorophenyl)sulfonyl]-5-methoxy-3-[(4-methyl-1-piperazinyl)methyl]-1H-indole dihydrochloride.

In another embodiment, the present invention relates to the combination of pure 5-$HT_6$ receptor antagonist, acetylcholinesterase inhibitor and NMDA receptor antagonist; wherein the pure 5-$HT_6$ receptor antagonist is 1-[(4-Isopropylphenyl)sulfonyl]-5-methoxy-3-[(4-methyl-1-piperazinyl)methyl]-1H-indole dihydrochloride.

In another embodiment, the present invention relates to the combination of 1-[(2-Bromophenyl)sulfonyl]-5-methoxy-3-[(4-methyl-1-piperazinyl)methyl]-1H-indole, donepezil and memantine or the pharmaceutically acceptable salt thereof.

In another embodiment, the present invention relates to the combination of 1-[(2-Bromophenyl)sulfonyl]-5-methoxy-3-[(4-methyl-1-piperazinyl)methyl]-1H-indole, rivastigmine and memantine or the pharmaceutically acceptable salt thereof.

In another embodiment, the present invention relates to the combination of 1-[(2-Bromophenyl)sulfonyl]-5-methoxy-3-[(4-methyl-1-piperazinyl)methyl]-1H-indole, galantamine and memantine or the pharmaceutically acceptable salt thereof.

In another embodiment, the present invention relates to the combination of 1-[(4-Fluorophenyl) sulfonyl]-5-methoxy-3-[(4-methyl-1-piperazinyl)methyl]-1H-indole, donepezil and memantine or the pharmaceutically acceptable salt thereof.

In another embodiment, the present invention relates to the combination of 1-[(4-Fluorophenyl) sulfonyl]-5-methoxy-3-[(4-methyl-1-piperazinyl)methyl]-1H-indole, rivastigmine and memantine or the pharmaceutically acceptable salt thereof.

In another embodiment, the present invention relates to the combination of 1-[(4-Fluorophenyl)sulfonyl]-5- methoxy-3-[(4-methyl-1-piperazinyl)methyl]-1H-indole, galantamine and memantine or the pharmaceutically acceptable salt thereof.

In another embodiment, the present invention relates to the combination of 1-[(4-Isopropylphenyl)sulfonyl]-5-methoxy-3-[(4-methyl-1-piperazinyl)methyl]-1H-indole, donepezil and memantine or the pharmaceutically acceptable salt thereof.

In another embodiment, the present invention relates to the combination of 1-[(4-Isopropylphenyl)sulfonyl]-5-methoxy-3-[(4-methyl-1-piperazinyl)methyl]-1H-indole, rivastigmine and memantine or the pharmaceutically acceptable salt thereof.

In another embodiment, the present invention relates to the combination of 1-[(4-Isopropylphenyl)sulfonyl]-5-methoxy-3-[(4-methyl-1-piperazinyl)methyl]-1H-indole, galantamine and memantine or the pharmaceutically acceptable salt thereof.

In another embodiment, the present invention relates to the combination of 1-[(2-Bromophenyl)sulfonyl]-5-methoxy-3-[(4-methyl-1-piperazinyl)methyl]-1H-indole dimesylate monohydrate, donepezil hydrochloride and memantine hydrochloride.

In another embodiment, the present invention relates to the combination of 1-[(2-Bromophenyl)sulfonyl]-5-methoxy-3-[(4-methyl-1-piperazinyl)methyl]-1H-indole dimesylate monohydrate, rivastigmine tartrate and memantine hydrochloride.

In another embodiment, the present invention relates to the combination of 1-[(2-Bromophenyl)sulfonyl]-5-methoxy-3-[(4-methyl-1-piperazinyl)methyl]-1H-indole dimesylate monohydrate, galantamine hydrobromide and memantine hydrochloride.

In another embodiment, the present invention relates to the combination of 1-[(4-Fluorophenyl)sulfonyl]-5-methoxy-3-[(4-methyl-1-piperazinyl)methyl]-1H-indole dihydrochloride, donepezil hydrochloride and memantine hydrochloride.

In another embodiment, the present invention relates to the combination of 1-[(4-Fluorophenyl)sulfonyl]-5-methoxy-3-[(4-methyl-1-piperazinyl)methyl]-1H-indole dihydrochloride, rivastigmine tartrate and memantine hydrochloride.

In another embodiment, the present invention relates to the combination of 1-[(4-Fluorophenyl)sulfonyl]-5-methoxy-3-[(4-methyl-1-piperazinyl)methyl]-1H-indole dihydrochloride, galantamine hydrobromide and memantine hydrochloride.

In another embodiment, the present invention relates to the combination of 1-[(4-Isopropylphenyl)sulfonyl]-5-methoxy-3-[(4-methyl-1-piperazinyl)methyl]-1H-indole dihydrochloride, donepezil hydrochloride and memantine hydrochloride.

In another embodiment, the present invention relates to the combination of 1-[(4-Isopropylphenyl)sulfonyl]-5-methoxy-3-[(4-methyl-1-piperazinyl)methyl]-1H-indole dihydrochloride, rivastigmine tartrate and memantine hydrochloride.

In another embodiment, the present invention relates to the combination of 1-[(4-Isopropylphenyl)sulfonyl]-5-methoxy-3-[(4-methyl-1-piperazinyl)methyl]-1H-indole dihydrochloride, galantamine hydrobromide and memantine hydrochloride.

In another embodiment, the present invention provides the combination of pure $5\text{-}HT_6$ receptor antagonist, acetylcholinesterase inhibitor and NMDA receptor antagonist which is more effective than the combination of pure $5\text{-}HT_6$ receptor antagonist and acetylcholinesterase inhibitor, acetylcholinesterase inhibitor and NMDA receptor antagonist or pure $5\text{-}HT_6$ receptor antagonist and NMDA receptor antagonist.

In another embodiment, the present invention provides the combination of the pure $5\text{-}HT_6$ receptor antagonist, acetylcholinesterase inhibitor and NMDA receptor antagonist which is more effective than the pure $5\text{-}HT_6$ receptor antagonist, acetylcholinesterase inhibitor and NMDA receptor antagonist alone.

In another embodiment, the present invention provides the combination of 1-[(2-Bromophenyl)sulfonyl]-5-methoxy-3-[(4-methyl-1-piperazinyl)methyl]-1H-indole dimesylate monohydrate, donepezil hydrochloride and memantine hydrochloride which is more effective than the combination of 1-[(2-Bromophenyl)sulfonyl]-5-methoxy-3-[(4-methyl-1-piperazinyl)methyl]-1H-indole dimesylate monohydrate and donepezil hydrochloride, donepezil hydrochloride and memantine hydrochloride or 1-[(2-Bromophenyl)sulfonyl]-5-methoxy-3-[(4-methyl-1-piperazinyl)methyl]-1H-indole dimesylate monohydrate and memantine hydrochloride.

In another embodiment, the present invention provides the combination of 1-[(2-Bromophenyl)sulfonyl]-5-methoxy-3-[(4-methyl-1-piperazinyl)methyl]-1H-indole dimesylate monohydrate, donepezil hydrochloride and memantine hydrochloride which is more effective than 1-[(2-Bromophenyl)sulfonyl]-5-methoxy-3-[(4-methyl-1-piperazinyl)methyl]-1H-indole dimesylate monohydrate, donepezil hydrochloride and memantine hydrochloride alone.

In another embodiment the pharmaceutically acceptable salt of pure $5\text{-}HT_6$ receptor antagonist includes but not limited to dimesylate monohydrate salt, dihydrochloride salt, oxalate salt, tartrate salt and the like. Preferably, the pharmaceutically acceptable salt is dimesylate monohydrate salt and dihydrochloride salt. More preferably, the pharmaceutically acceptable salt is dimesylate monohydrate salt.

In another embodiment, the present invention relates to a method of treating Alzheimer's disease comprising administering to a patient in need thereof a therapeutically effective amount of the said combination.

In another embodiment, the present invention relates to a method of treating Alzheimer's disease comprising administering to a patient in need thereof a therapeutically effective amount of 1-[(2-Bromophenyl) sulfonyl]-5-methoxy-3-[(4-methyl-1-piperazinyl)methyl]-1H-indole or a pharmaceutically acceptable salt thereof, acetylcholinesterase inhibitor and NMDA receptor antagonist.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole or a pharmaceutically acceptable salt thereof, acetylcholinesterase inhibitor and NMDA receptor antagonist.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole or a pharmaceutically acceptable salt thereof, acetylcholinesterase inhibitor and NMDA receptor antagonist.

In another embodiment, the present invention relates to a method of treating Alzheimer's disease comprising administering to a patient in need thereof a therapeutically effective amount of 1-[(2-Bromophenyl) sulfonyl]-5-methoxy-3-

[(4-methyl-1-piperazinyl)methyl]-1H-indole or a pharmaceutically acceptable salt thereof in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole or a pharmaceutically acceptable salt thereof in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole or a pharmaceutically acceptable salt thereof in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole dimesylate monohydrate in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole dihydrochloride in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole dihydrochloride in combination with acetylcholinesterase inhibitor and NMDA receptor antagonist.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole dimesylate monohydrate in combination with donepezil or a pharmaceutically acceptable salt thereof and memantine or a pharmaceutically acceptable salt thereof.

In another embodiment, the present invention relates to a method of treating Alzheimer's disease comprising administering to a patient in need thereof a therapeutically effective amount of 1-[(2-Bromophenyl)sulfonyl]-5-methoxy-3-[(4-methyl-1-piperazinyl)methyl]-1H-indole dimesylate monohydrate in combination with donepezil hydrochloride and memantine hydrochloride.

In another embodiment, the present invention relates to the combination of 1-[(2-Bromophenyl)sulfonyl]-5-methoxy-3-[(4-methyl-1-piperazinyl)methyl]-1H-indole dimesylate monohydrate, acetylcholinesterase inhibitor and NMDA receptor antagonist for use in the treatment of Alzheimer's disease.

In yet another aspect, the present invention relates to 1-[(2-Bromophenyl)sulfonyl]-5-methoxy-3-[(4-methyl-1-piperazinyl)methyl]-1H-indole or a pharmaceutically acceptable salt thereof for use in the adjunct treatment of Alzheimer's disease in a patient on treatment with acetylcholinesterase inhibitor and NMDA receptor antagonist.

In yet another aspect, the present invention relates to 1-[(4-Fluorophenyl)sulfonyl]-5-methoxy-3-[(4-methyl-1-piperazinyl)methyl]-1H-indole or a pharmaceutically acceptable salt thereof for use in the adjunct treatment of Alzheimer's disease in a patient on treatment with acetylcholinesterase inhibitor and NMDA receptor antagonist.

In yet another aspect, the present invention relates to 1-[(4-Isopropylphenyl)sulfonyl]-5-methoxy-3-[(4-methyl-1-piperazinyl)methyl]-1H-indole or a pharmaceutically acceptable salt thereof for use in the adjunct treatment of Alzheimer's disease in a patient on treatment with acetylcholinesterase inhibitor and NMDA receptor antagonist.

In another embodiment, the present invention relates to 1-[(2-Bromophenyl)sulfonyl]-5-methoxy-3-[(4-methyl-1-piperazinyl)methyl]-1H-indole dimesylate monohydrate for use in the adjunct treatment of Alzheimer's disease in a patient on treatment with donepezil and memantine or a pharmaceutically acceptable salt thereof.

In another embodiment, the present invention relates to 1-[(4-Fluorophenyl) sulfonyl]-5-methoxy-3-[(4-methyl-1-piperazinyl)methyl]-1H-indole dihydrochloride for use in the adjunct treatment of Alzheimer's disease in a patient on treatment with donepezil and memantine or a pharmaceutically acceptable salt thereof.

In another embodiment, the present invention relates to 1-[(4-Isopropylphenyl)sulfonyl]-5-methoxy-3-[(4-methyl-1-piperazinyl)methyl]-1H-indole dihydrochloride for use in the adjunct treatment of Alzheimer's disease in a patient on treatment with donepezil and memantine or a pharmaceutically acceptable salt thereof.

In another embodiment, the present invention relates to use of the combination of pure 5-$HT_6$ receptor antagonist, acetylcholinesterase inhibitor and NMDA receptor antagonist in the manufacture of a medicament for treatment of Alzheimer's disease.

In another embodiment, the present invention relates to use of pure 5-$HT_6$ receptor antagonist in the manufacture of a medicament for treatment of Alzheimer's disease in combination with acetylcholinesterase inhibitor and NMDA receptor antagonist.

In another embodiment, the present invention relates to use of pure 5-$HT_6$ receptor antagonist in the manufacture of a medicament for treatment of Alzheimer's disease as adjunct to acetylcholinesterase inhibitor and NMDA receptor antagonist.

In another embodiment, the present invention relates to use of the 1-[(2-Bromophenyl)sulfonyl]-5-methoxy-3-[(4-methyl-1-piperazinyl)methyl]-1H-indole or a pharmaceutically acceptable salt thereof in the manufacture of a medicament for treatment of Alzheimer's disease in combination with donepezil or a pharmaceutically acceptable salt thereof and memantine or a pharmaceutically acceptable salt thereof.

In another embodiment, the present invention relates to use of the 1-[(2-Bromophenyl)sulfonyl]-5-methoxy-3-[(4-methyl-1-piperazinyl)methyl]-1H-indole dimesylate monohydrate in the manufacture of a medicament for treatment of Alzheimer's disease in combination with donepezil or a pharmaceutically acceptable salt thereof and memantine or a pharmaceutically acceptable salt thereof.

In another embodiment, the present invention relates to use of the 1-[(2-Bromophenyl)sulfonyl]-5-methoxy-3-[(4-methyl-1-piperazinyl)methyl]-1H-indole dimesylate monohydrate in the manufacture of a medicament for treatment of Alzheimer's disease in combination with donepezil hydrochloride and memantine hydrochloride.

In another embodiment, the present invention relates to pure 5-HT$_6$ receptor antagonist for use in the treatment of Alzheimer's disease in combination with Namzaric®.

In another embodiment, the present invention relates to a method of treating Alzheimer's disease comprising administering to a patient in need thereof a therapeutically effective amount of the pure 5-HT$_6$ receptor antagonist in combination with Namzaric®.

In another embodiment, the present invention relates to the combination for treatment of Alzheimer's disease, wherein Alzheimer's disease is mild Alzheimer's disease.

In another embodiment, the present invention relates to the combination for treatment of Alzheimer's disease, wherein the Alzheimer's disease is moderate Alzheimer's disease.

In another embodiment, the present invention relates to the combination for treatment of Alzheimer's disease, wherein the Alzheimer's disease is severe Alzheimer's disease.

In another embodiment, the present invention relates to the combination wherein the active ingredients can be administered to a patient concurrently or separately.

In yet another aspect, the active ingredients of the combination of the present invention are normally administered by formulating the active ingredients into a pharmaceutical composition in accordance with standard pharmaceutical practice.

In yet another aspect, the active ingredients of the combination of the present invention may be administered by oral, nasal, local, dermal or parenteral routes.

In yet another aspect, the active ingredients of the combination of the present invention can be administered by the same or different route of administration. For instance, the 5-HT$_6$ receptor antagonist of the instant invention can be administered orally, the acetylcholinesterase inhibitor can be administered transdermally and the NMDA receptor antagonist can be administered locally.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

In yet another aspect, the pharmaceutical composition of the combination of the instant invention can be conventional formulations such as immediate release formulations, modified release formulations such as sustained release formulations, delayed release formulations and extended release formulations or new delivery systems such as oral disintegrating formulations and transdermal patches.

The dose of the active compounds can vary depending on factors such as age and weight of patient, nature, route of administration and severity of the disease to be treated and such other factors. Therefore, any reference regarding pharmacologically effective amount of the compounds 1, 2 and 3 refers to the aforementioned factors.

In yet another aspect, the 5-HT$_6$ receptor antagonist can be co-administered with acetylcholinesterase inhibitor and NMDA receptor antagonist at a daily dose of 1 mg to 300 mg; such as 1, 5, 10, 20, 25, 30, 50, 75, 100, 150, 200 or 300 mg, preferably at a daily dose of 10, 25, 30, 50, 75, 100, 125 or 150 mg and most preferably at a daily dose of 10, 25, 50, 75, 100 or 125 mg.

In yet another aspect, the acetylcholinesterase inhibitor can be co-administered with 5-HT$_6$ receptor antagonist and NMDA receptor antagonist at a daily dose of 1 mg to 30 mg; such as 1, 1.5, 2, 3, 4, 4.5, 5, 6, 8, 9.5, 10, 12, 13, 13.3, 15, 16, 23, 24, 25 or 30 mg, preferably at a daily dose of 1, 1.5, 2, 3, 4, 4.5, 5, 6, 8, 9.5, 10, 12, 13, 13.3, 16, 23, 24, or 25 mg and most preferably at a daily dose of 1.5, 3, 4, 4.5, 5, 6, 8, 9.5, 10, 12, 13.3, 16, 23 or 24 mg.

In yet another aspect, the NMDA receptor antagonist, memantine can be co-administered with 5-HT$_6$ receptor antagonist and acetylcholinesterase inhibitor at a daily dose of 1 mg to 40 mg; such as 5, 10, 14, 20, 28 or 40 mg, preferably at a daily dose of 5, 10, 14, 20 or 28 mg and most preferably at a daily dose of 5, 7, 10, 14, 20 or 28 mg.

In yet another aspect, the acetylcholinesterase inhibitor, donepezil can be co-administered with 5-HT$_6$ receptor antagonist and NMDA receptor antagonist at a daily dose of 2 mg to 30 mg; such as 2, 5, 10, 15, 23, 25 or 30 mg, preferably at a daily dose of 2, 5, 10, 23 or 25 mg and most preferably at a daily dose of 5, 10 or 23 mg.

In yet another aspect, the acetylcholinesterase inhibitor, rivastigmine can be co-administered with 5-HT$_6$ receptor antagonist and NMDA receptor antagonist at a daily dose of 0.5 mg to 15 mg; such as 1, 1.5, 3, 4.5, 5, 6, 9.5, 10 or 13.3 mg, preferably at a daily dose of 1, 1.5, 3, 4.5, 5, 6, 9.5 or 13.3 mg and most preferably at a daily dose of 1.5, 3, 4.5, 6, 9.5 and 13.3 mg.

In yet another aspect, the acetylcholinesterase inhibitor, galantamine can be co-administered with 5-HT$_6$ receptor antagonist and NMDA receptor antagonist at a daily dose of 1 mg to 30 mg; such as 1, 2, 4, 6, 8, 12, 16, 24 and 30 mg, preferably at a daily dose of 2, 4, 6, 8, 12, 16 and 24 mg and most preferably at a daily dose of 4, 8, 12, 16 and 24 mg.

In yet another aspect, the treatment comprises administering to the patient 1 mg to 200 mg of 1-[(2-Bromophenyl)

sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 10 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 125 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 150 mg to 200 mg of 1-[(2-Bromophenyl)sulfonyl]-5-methoxy-3-[(4-methyl-1-piperazinyl) methyl]-1H-indole or a pharmaceutically acceptable salt thereof, per day.

In yet another aspect, the treatment comprises administering to the patient 10 mg to 100 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 10 mg to 50 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 50 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 75 mg to 100 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 25 mg of donepezil or a pharmaceutically acceptable salt thereof, per day.

In yet another aspect, the treatment comprises administering to the patient 5 mg to 25 mg of donepezil or a pharmaceutically acceptable salt thereof, per day.

In yet another aspect, the treatment comprises administering to the patient, 5, 10 or 23 mg of donepezil or a pharmaceutically acceptable salt thereof, per day.

In yet another aspect, the treatment comprises administering to the patient 1 mg to 40 mg of memantine or a pharmaceutically acceptable salt thereof, per day.

In yet another aspect, the treatment comprises administering to the patient 5 mg to 30 mg of memantine or a pharmaceutically acceptable salt thereof, per day.

In yet another aspect, the treatment comprises administering to the patient 5, 10, 14, 20 or 28 mg of memantine or a pharmaceutically acceptable salt thereof, per day.

In yet another aspect, the treatment comprises administering the active compounds to the patient one to three times per day, one to three times per week or one to three times per month. Preferably, the treatment comprises administering the compound to a patient once a day, twice a day, or thrice a day. More preferably, the treatment comprises administering the compound to a patient once a day.

EXAMPLES

The examples given below are provided by the way of illustration only and therefore should not be construed to limit the scope of the invention.

Abbreviations $5\text{-HT}_{1A}$: 5-Hydroxytryptamine 1A receptor
$5\text{-HT}_{1B}$: 5-Hydroxytryptamine 1B receptor
$5\text{-HT}_{1D}$: 5-Hydroxytryptamine 1D receptor
$5\text{-HT}_{2A}$: 5-Hydroxytryptamine 2A receptor
$5\text{-HT}_{2C}$: 5-Hydroxytryptamine 2C receptor
$5\text{-HT}_{4}$: 5-Hydroxytryptamine 4 receptor
$5\text{-HT}_{5A}$: 5-Hydroxytryptamine 5A receptor
$5\text{-HT}_{6}$: 5-Hydroxytryptamine 6 receptor
$5\text{-HT}_{7}$: 5-Hydroxytryptamine 7 receptor
ANOVA: Analysis of variance
AP: Anterior Posterior
aCSF: Artificial Cerebrospinal fluid
cAMP: Cyclic adenosine monophosphate
$CaCl_2.2H_2O$: Calcium Chloride dehydrate
DV: Dorsal Ventral
$EC_{50}$: Half maximal effective concentration
EDTA: Ethylenediaminetetraacetic acid
EEG: Electroencephalogram
GPCR: G-Protein Coupled Receptor
HCl: Hydrochloric acid
h: Hour (s)
i.p.: Intraperitoneal
i.v.: Intravenous
KCl: Potassium chloride
$K_b$: Binding constant
$K_i$: Inhibitory constant
LC-MS/MS: Liquid chromatography-Mass spectrometry/ Mass spectrometry
mg: Milligram
$MgCl_2$: Magnesium chloride
min: Minute (s)
ML: Medial Lateral
mM: Millimolar
nmol/L: Nanomoles per litre
NaCl: Sodium chloride
$NaH_2PO_4.2H_2O$: Sodium dihydrogen phosphate dihydrate
$Na_2HPO_4.7H_2O$: Sodium monohydrogen phosphate heptahydrate
NPO: Nucleus Pontis Oralis
nM: Nanomolar
p.o.: Per oral
s.c.: Subcutaneous
S.E.M.: Standard error of the mean
µM: Micromolar
θ: Theta Example 1

Determination of $K_b$ Values at $5\text{-HT}_6$ Receptor:

A stable CHO cell line expressing recombinant human $5\text{-HT}_6$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 10 µM of serotonin in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in reducing the luciferase activity by 50%. The $K_b$ values were calculated by feeding the concentration of agonist used in the assay and its $EC_{50}$ value in the same software.

References: *Molecular Brain Research*, 2001, 90, 110-117 and *British Journal of Pharmacology*, 2006, 148, 1133-1143.

Results:

Compounds 1, 2 and 3 exhibit antagonistic activity in CRE-Luc based reporter gene assay on human recombinant 5-$HT_6$ receptor with no detectable agonist activity. The $K_b$ values tabulated below are average of three independent experiments.

| S. No | Example | $K_b$ (nM) |
|---|---|---|
| 1 | Compound 1 | 4.2 ± 0.9 |
| 2 | Compound 2 | 7.2 ± 1.8 |
| 3 | Compound 3 | 1.6 ± 0.3 |

Example 2

Determination of $K_i$ Value at 5-$HT_6$ Receptor

Compound was tested at MDS pharma services and Novascreen according to the following procedures.

Materials and Methods:
Receptor source: Human recombinant expressed in Hela cells
Radioligand: [$^3$H]-LSD (60-80 Ci/mmol)
Final ligand concentration—[1.5 nM]
Non-Specific Ligand: 5 µM Serotonin (5-HT)
Reference compound: Methiothepin mesylate
Positive control: Methiothepin mesylate
Incubation conditions: Reactions were carried out in 50 mM Tris-HCl (pH 7.4) containing 10 mM $MgCl_2$, 0.5 mM EDTA for 60 minutes at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-$HT_6$ binding site.

Reference: *Molecular Pharmacology*, 1993, 43, 320-327.

Results:

Compounds 1, 2 and 3 selectively bind to 5-$HT_6$ receptor when tested by the in-vitro radioligand binding technique on human recombinant 5-$HT_6$ receptor. The $K_i$ values are tabulated below.

| S. No | Example | $K_i$ (nM) |
|---|---|---|
| 1 | Compound 1 | 2.04 |
| 2 | Compound 2 | 4.96 |
| 3 | Compound 3 | 3.67 |

Example 3

Determination of $K_i$ Value at 5-$HT_{2A}$ Receptor

Compound was tested according to the following procedures.

Materials and Methods:
Receptor source: Recombinant mammalian cells
Radioligand: [$^3$H]-Ketanserine (47.3 Ci/mmol)
Final ligand concentration—[1.75 nM]
Non-Specific Ligand: 0.1 mM 1-Naphthylpiperazine (1-NP)
Reference compound: 1-Naphthylpiperazine (1-NP)
Positive control: 1-Naphthylpiperazine (1-NP)
Incubation conditions: Reactions were carried out in 67 mM Tris-HCl (pH 7.4) for 1 hour at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-$HT_{2A}$ binding site.

Reference: *Methods in Molecular Biology*, 2002, 190, 31-49

Results:

Compounds 1, 2 and 3 bind weakly to 5-$HT_{2A}$ receptor when tested by the in-vitro radioligand binding technique on human recombinant 5-$HT_{2A}$ receptor. The $K_i$ values tabulated below are average of three independent experiments.

| S. No | Example | $K_i$ |
|---|---|---|
| 1 | Compound 1 | 2514 ± 377 nM |
| 2 | Compound 2 | >10 µM |
| 3 | Compound 3 | 926 ± 317 nM |

Example 4

Test compounds were also evaluated for their 5-$HT_6$ receptor selectivity over closely related serotonin subtypes like 5-$HT_{1A}$, 5-$HT_{1B}$, 5-$HT_{1D}$, 5-$HT_{2A}$, 5-$HT_{2C}$, 5-$HT_4$, 5-$HT_{5A}$ and 5-$HT_7$ in commercial panel at Novascreen.

Compounds 1, 2 and 3 have shown selectivity of more than 250-fold over these receptor subtypes.

Example 5

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) in the absence of any objects on day 1.

Rats received vehicle or donepezil and memantine or test compounds, donepezil and memantine on the day of habituation, before familiar ($T_1$) and choice ($T_2$) trials. During the familiarization phase ($T_1$), the rats were placed individually in the arena for 3 minutes, in which two identical objects ($a_1$ and $a_2$) were positioned 10 cm from the wall. 24 hours after $T_1$, trial for long-term memory test was assessed. The same rats were placed in the same arena as they were placed in $T_1$ trial. During the choice phase ($T_2$) rats were allowed to explore the arena for 3 minutes in presence of a copy of familiar object (a₃) and one novel object (b). During the T₁ and T₂ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).

$T_2$ is the total time spent exploring the familiar object and novel object (a3+b).

Discriminative index is ratio of time spent exploring the novel object divided by sum of time spent exploring the novel object and familiar object in choice trial ($T_2$).

The object recognition test was performed as described in *Behavioural Brain Research*, 1988, 31, 47-59.

Figure 1A:
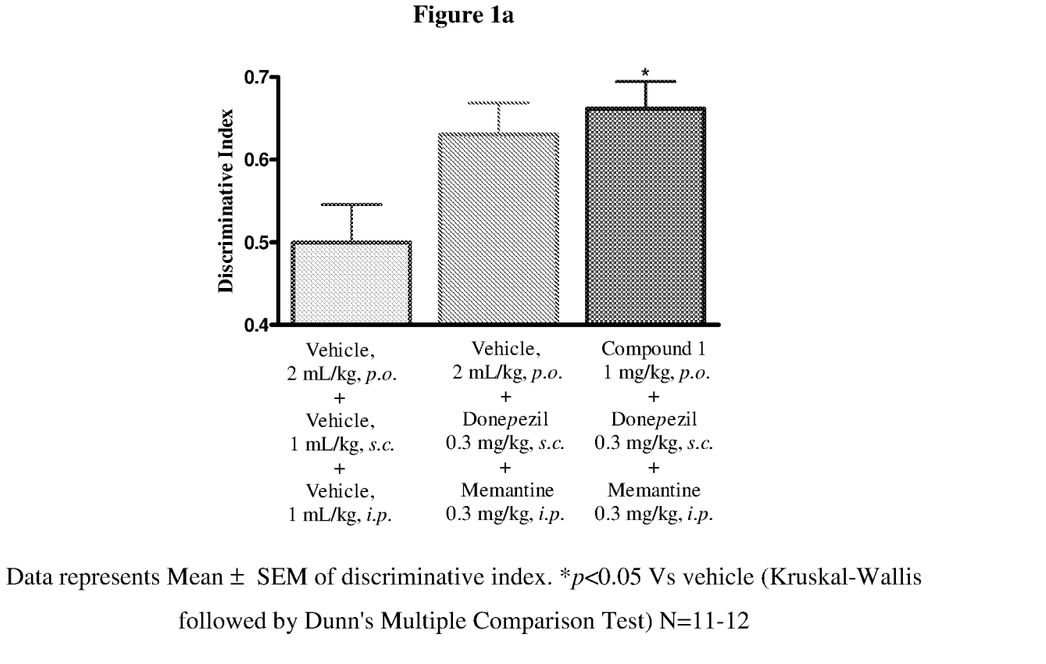
FIG. 1a depicts the results of the effect of a co-treatment of compound 1 with donepezil and memantine on cognition enhancing properties using object recognition task model.
Figure 1B:
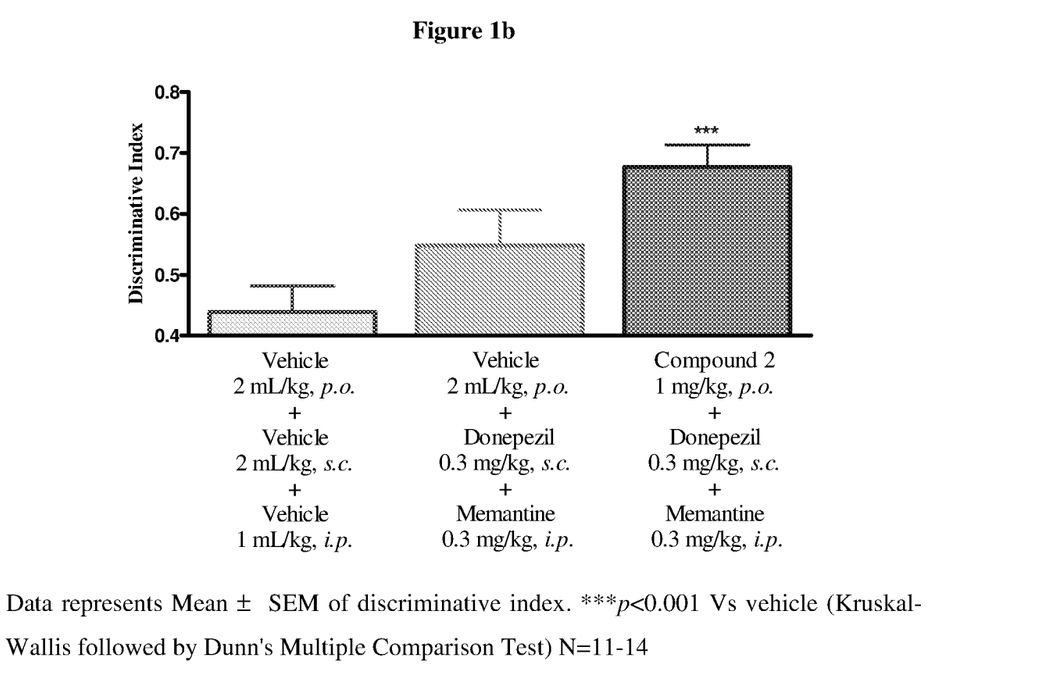
FIG. 1b depicts the results of the effect of a co-treatment of compound 2 with donepezil and memantine on cognition enhancing properties using object recognition task model.
Figure 1C:
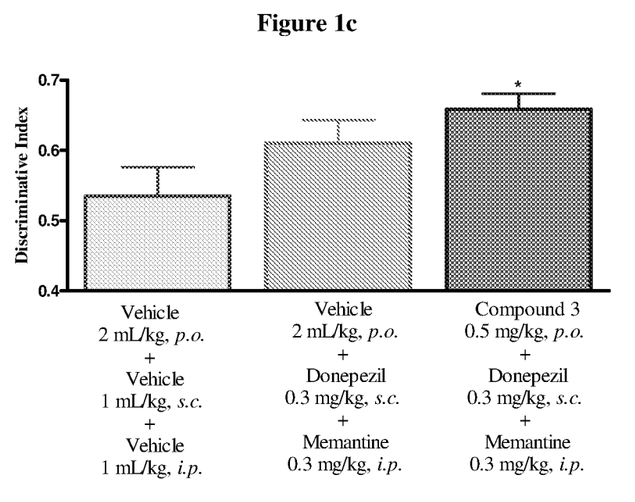
FIG. 1c depicts the results of the effect of a co-treatment of compound 3 with donepezil and memantine on cognition enhancing properties using object recognition task model.

Results:

No significant increase in discriminative index was observed in the group treated with donepezil and memantine when compared to the vehicle treatment. However the group co-treated with test compounds, donepezil and memantine showed significant improvement in the memory end point (discriminative index). The results of this study are provided in FIG. 1a-1c.

Example 6

Evaluation of Acetylcholine Modulation in Ventral Hippocampus of Male Wistar Rats Experimental Procedure Male Wistar rats (240-300 g body weight) were stereotaxically implanted with a microdialysis guide cannula in ventral hippocampus (AP: −5.2 mm, ML: +5.0 mm, DV: −3.8 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglas bowl with free access to feed and water.

After surgical recovery of 4-5 days, male Wistar rats were connected to dual quartz lined two-channel liquid swivel (Instech, UK) on a counter balance lever arm, which allowed unrestricted movements of the animal. Sixteen hours before start of study, a pre-equilibrated microdialysis probe (4 mm dialysis membrane) was inserted into the ventral hippocampus through the guide cannula. On the day of study, probe was perfused with artificial cerebrospinal fluid (aCSF; NaCl 147 mM, KCl3 mM, $MgCl_2$ 1 mM, $CaCl_2.2H_2O$ 1.3 mM, $NaH_2PO_4.2H_2O$ 0.2 mM and $Na_2HPO_4.7H_2O$ 1 mM, pH 7.2) at a flow rate of 1.5 μL/min and a stabilization period of 2 h was maintained. Five basal samples were collected at 20 min intervals prior to the treatment of test compounds (1 or 3 mg/kg, p.o.) or vehicle. Donepezil (1 mg/kg, s.c.) and memantine (1 mg/kg, s.c.) were administered 30 min after administration of test compounds. Dialysate samples were collected for an additional period of 4 hours post treatment of test compounds. Dialysates were stored below −50° C. prior to analysis.

Acetylcholine in dialysate was quantified using LC-MS/MS method in the calibration range of 0.103-103.491 nmol/L.

All microdialysis data for acetylcholine was plotted as percent change from mean dialysate basal concentrations with 100% defined as the average of five pre-dose values. The percent change in acetylcholine levels were compared with donepezil and memantine combination using two-way analysis of variance (time and treatment), followed by Bonferroni's posttest. Area under the curve (AUC) values for percent change in acetylcholine levels were calculated and the statistical significance between the mean AUC value were compared against donepezil and memantine treatment using one-way ANOVA followed by Dunnett's test. Statistical significance was considered at a p value less than 0.05. Incorrect probe placement was considered as criteria to reject the data from animal.

Reference: Paxinos G. and Watson C. (2004) Rat brain in stereotaxic coordinates. Academic Press, New York Results:

Compound 1

Treatment with donepezil (1 mg/kg, s.c.) and memantine (1 mg/kg, s.c.) produced increase in hippocampal acetylcholine levels to the maximum of 1204±106% of basal levels. Compound 1 produced dose dependent increase of acetylcholine in combination with donepezil (1 mg/kg, s.c.) and memantine (1 mg/kg, s.c.). The increase in acetylcholine after combination of compound 1, donepezil and memantine was significantly higher compared to donepezil and memantine combination. Mean maximum increase in acetylcholine was observed to be 1383±194 and 2136±288% of pre-dose levels after 1 and 3 mg/kg, p.o., combinations, respectively (FIG. 2 (a)).

Figure 2:
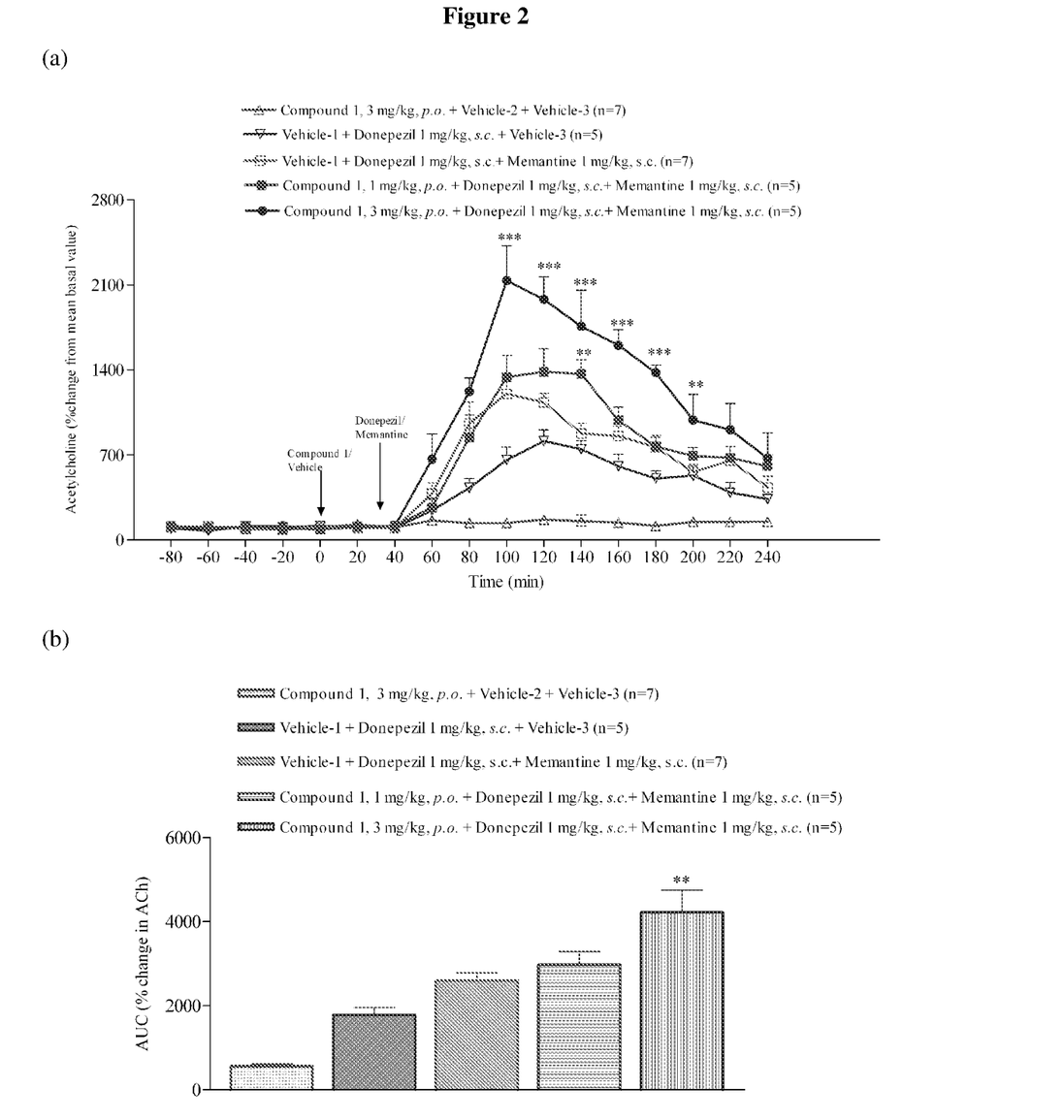
FIG. 2 depicts the effect of compound 1 alone and in combination with donepezil and memantine on extracellular levels of acetylcholine in ventral hippocampus of male Wistar rats.

Mean area under the curve values (AUC) calculated after treatment of compound 1 (3 mg/kg, p.o.), donepezil (1 mg/kg, s.c.) and memantine (1 mg/kg, s.c.) were significantly higher compared to donepezil (1 mg/kg, s.c.) and memantine (1 mg/kg, s.c.) combination (FIG. 2 (b)).

Compound 2

Treatment with donepezil (1 mg/kg, s.c.) and memantine (1 mg/kg, s.c.) produced increase in hippocampal acetylcholine levels to the maximum of 691±148% of basal levels. The increase in acetylcholine after combination of compound 2 (3 mg/kg, p.o.), donepezil (1 mg/kg, s.c.) and memantine (1 mg/kg, s.c.) was significantly higher compared to donepezil and memantine combination with mean maximum increase of 1776±365% above pre-dose levels (FIG. 3 (a)).

Figure 3:
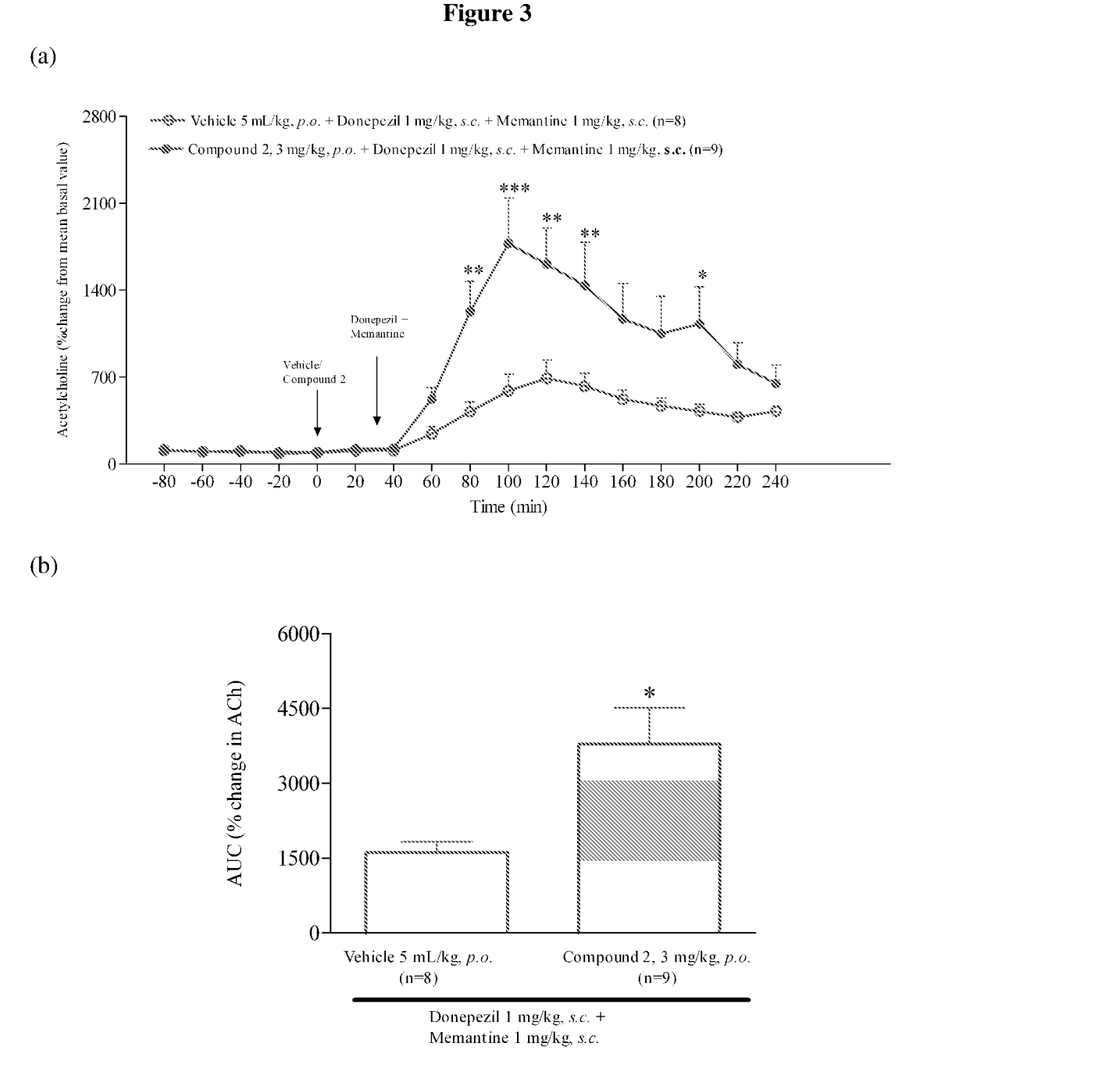
FIG. 3 depicts the effect of compound 2, donepezil and memantine combination on extracellular levels of acetylcholine in ventral hippocampus of male Wistar rats.

Mean area under the curve value (AUC) calculated after treatment of compound 2 (3 mg/kg, p.o.), donepezil (1 mg/kg, s.c.) and memantine (1 mg/kg, s.c.) combination was significantly higher compared to donepezil (1 mg/kg, s.c.) and memantine (1 mg/kg, s.c.) combination (FIG. 3 (b)).

Compound 3

Treatment with donepezil (1 mg/kg, s.c.) and memantine (1 mg/kg, s.c.) produced increase in hippocampal acetylcholine levels to the maximum of 691±148% of basal levels. The increase in acetylcholine after combination of compound 3 (3 mg/kg, p.o.), donepezil (1 mg/kg, s.c.) and memantine (1 mg/kg, s.c.) was significantly higher compared to donepezil and memantine combination with mean maximum increase of 1141±258% above pre-dose levels (FIG. 4 (a)).

Figure 4:
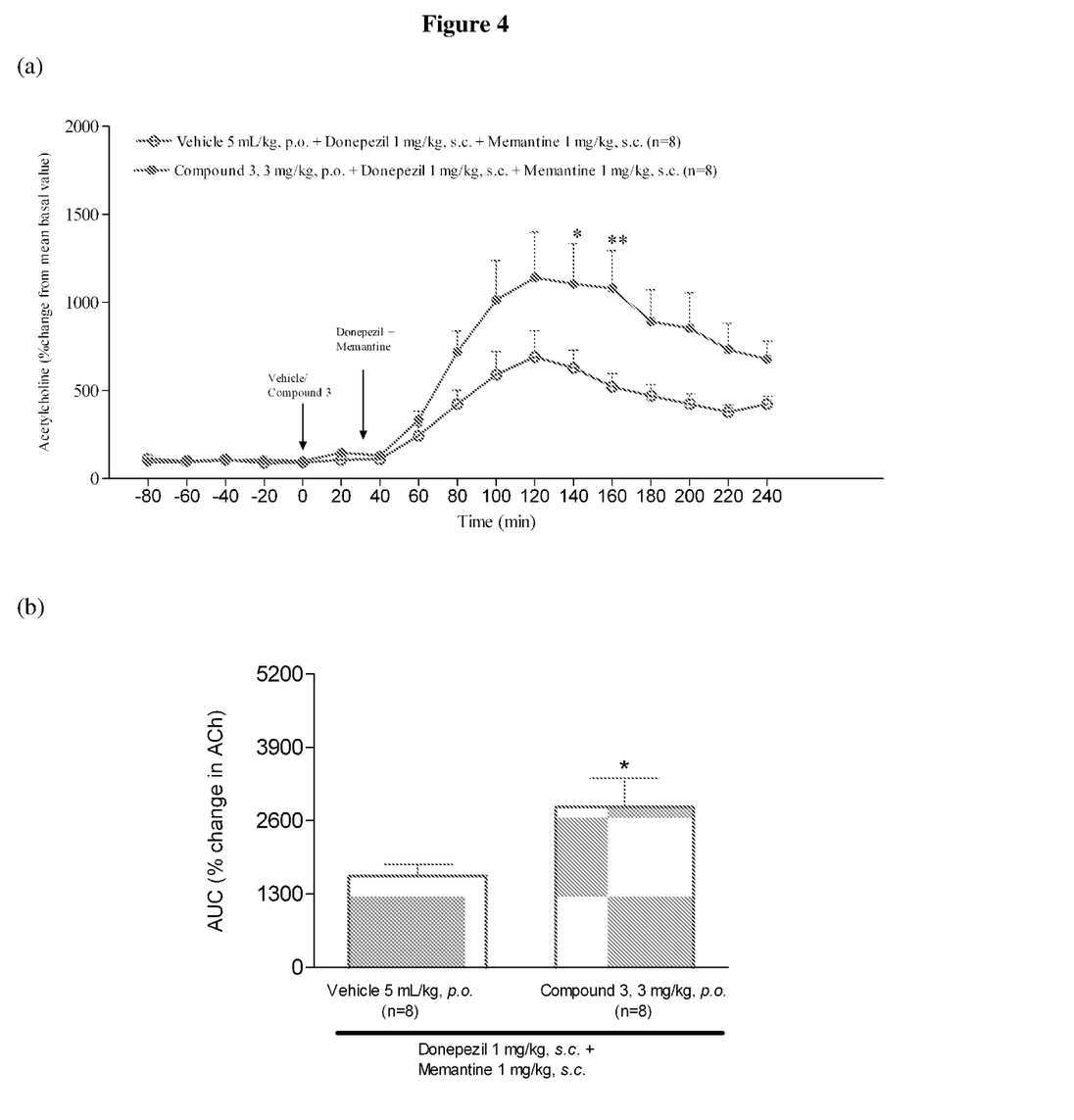
FIG. 4 depicts the effect of compound 3, donepezil and memantine combination on extracellular levels of acetylcholine in ventral hippocampus of male Wistar rats.

Mean area under the curve value (AUC) calculated after treatment of compound 3 (3 mg/kg, p.o.), donepezil (1 mg/kg, s.c.) and memantine (1 mg/kg, s.c.) combination was significantly higher compared to donepezil (1 mg/kg, s.c.) and memantine (1 mg/kg, s.c.) combination (FIG. 4 (b)).

Example 7

Evaluation of Theta Modulation in Dorsal Hippocampus of Anesthetized Male Wistar Rats Synchronous hippocampal EEG activity occurring in θ rhythm (frequency range of 4 to 8 Hz) has been associated with mnemonic processes in vivo.

Experimental Procedure

Male Wistar rats (240-320 g) were anesthetized with 1.2 to 1.5 g/kg urethane intraperitoneally, under anesthesia a catheter was surgically implanted in the left femoral vein for administration of drugs. After cannulation, the animal was placed in a stereotaxic frame for implanting an electrode (stainless steel wire, Plastics One) into the dorsal hippocampus (AP, −3.8 mm; ML, +2.2 mm; DV, −1.5 mm from dura; Paxinos and Watson, 1994) and bipolar stimulating electrode (untwisted stainless steel wires, separated by 0.75-1.0 mm at their tips, Plastics One) was implanted in the NPO (AP, −7.8 mm; ML, ±1.8 mm; DV, −6.0 mm; Paxinos and Watson, 1994). Additionally one electrode was implanted into the cerebellum which served as a reference. Hippocampal θ rhythm was evoked via a 6-s electrical stimulation train (20-160 μA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore (Version 3.0). Baseline amplitude level was achieved by using the current required to elicit θ rhythm to 50% of the maximal amplitude under control conditions. After the stabilization period of one hour, Baseline recording was done for 30 min followed by the treatment of vehicle or compound 1 (1 mg/kg, i.v.). Donepezil (0.3 mg/kg, i.v.) and memantine (0.3 mg/kg, i.v.) was administered 30-min after compound 1 treatment and recording was continued for additional 1 hour.

Power in the θ frequency in the stimulation period during the 30 minutes baseline period was calculated and the percent changes in these measures post treatment were calculated. The percent change in relative θ power after combination treatment of compound 1, donepezil and memantine was compared with donepezil and memantine using two-way analysis of variance (time and treatment), followed by Bonferroni's posttest. Statistical significance was considered at a p value less than 0.05.

Figure 5:
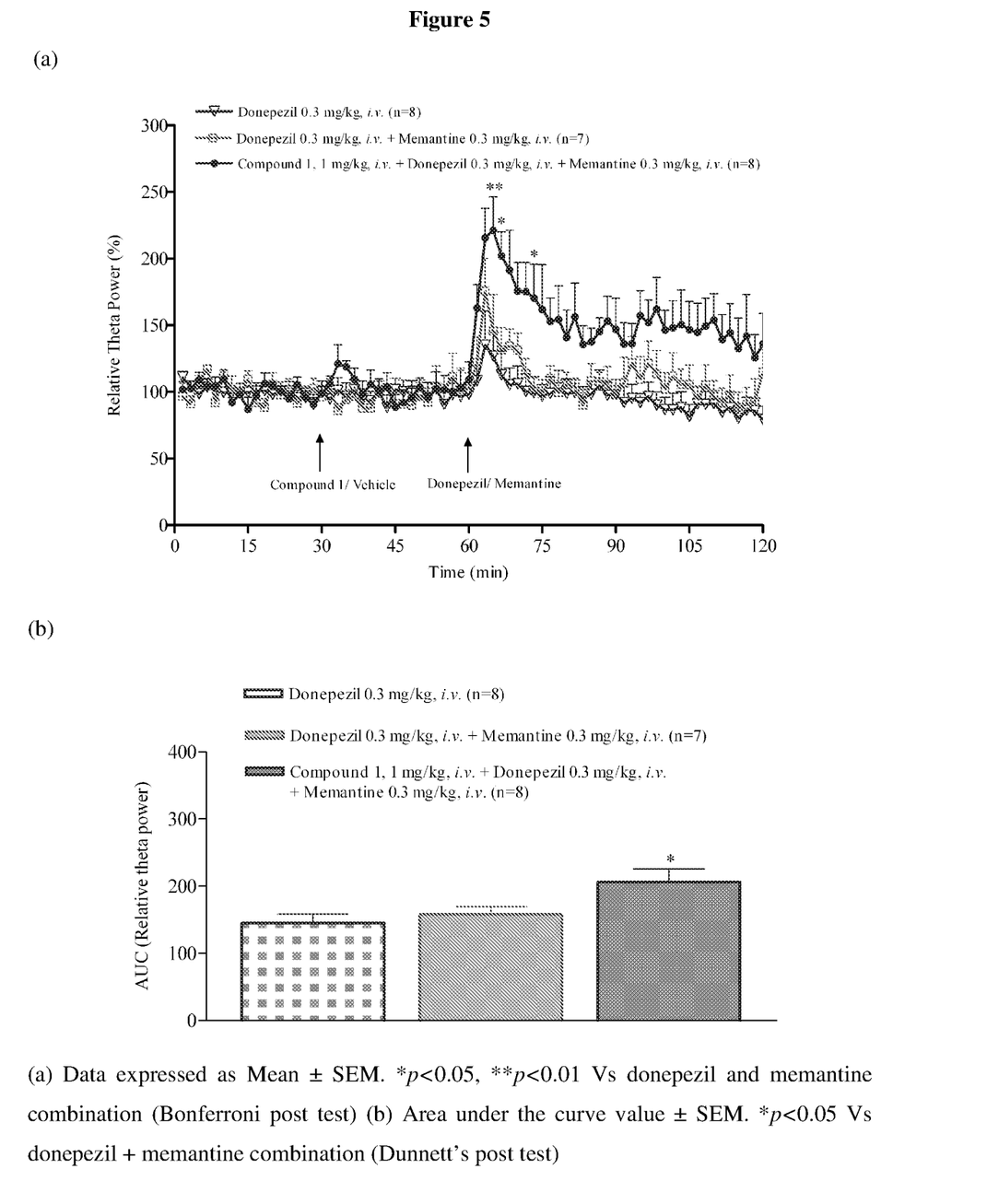
FIG. 5 depicts the effect of compound 1, donepezil and memantine combination on evoked theta modulation in dorsal hippocampus of anesthetized male Wistar rats.

Reference: Paxinos G. and Watson C. (2004) Rat brain in stereotaxic coordinates. Academic Press, New York Results:

Treatment with donepezil (0.3 mg/kg, i.v.) and memantine (0.3 mg/kg, i.v.) combination produced about 176±25% increases in hippocampal θ power. Compound 1 (1 mg/kg, i.v.) in combination with donepezil (0.3 mg/kg, i.v.) and memantine (0.3 mg/kg, i.v.) produced significant increase in θ power levels and peak levels reached up to 221±25% of pre-dose levels (FIG. 5).

We claim:

1. A combination comprising pure $5\text{-HT}_6$ receptor antagonist, acetylcholinesterase inhibitor and NMDA receptor antagonist, wherein the pure $5\text{-HT}_6$ receptor antagonist is selected from the group consisting of:
   1-[(2-Bromophenyl)sulfonyl]-5-methoxy-3-[(4-methyl-1-piperazinyl)methyl]-1H-indole;
   1-[(4-Fluorophenyl)sulfonyl]-5-methoxy-3-[(4-methyl-1-piperazinyl)methyl]-1H-indole; and
   1-[(4-Isopropylphenyl)sulfonyl]-5-methoxy-3-[(4-methyl-1-piperazinyl)methyl]-1H-indole;
   or a pharmaceutically acceptable salt thereof;
   the acetylcholinesterase inhibitor is donepezil or a pharmaceutically acceptable salt thereof; and
   the NMDA receptor antagonist is memantine or a pharmaceutically acceptable salt thereof.

2. The combination as claimed in claim 1, wherein the pure $5\text{-HT}_6$ receptor antagonist is 1-[(2-Bromophenyl)sulfonyl]-5-methoxy-3-[(4-methyl-1-piperazinyl)methyl]-1H-indole or a pharmaceutically acceptable salt thereof.

3. The combination as claimed in claim 1, wherein the pharmaceutically acceptable salt of the pure $5\text{-HT}_6$ receptor antagonist is,
   1-[(2-Bromophenyl)sulfonyl]-5-methoxy-3-[(4-methyl-1-piperazinyl)methyl]-1H-indole dimesylate monohydrate;
   1-[(4-Fluorophenyl)sulfonyl]-5-methoxy-3-[(4-methyl-1-piperazinyl)methyl]-1H-indole dihydrochloride; or
   1-[(4-Isopropylphenyl)sulfonyl]-5-methoxy-3-[(4-methyl-1-piperazinyl)methyl]-1H-indole dihydrochloride.

4. The combination as claimed in claim 3, wherein the pure $5\text{-HT}_6$ receptor antagonist is 1-[(2-Bromophenyl)sulfonyl]-5-methoxy-3-[(4-methyl-1-piperazinyl)methyl]-1H-indole dimesylate monohydrate.

5. The combination as claimed in claim 1, wherein the acetylcholinesterase inhibitor is donepezil hydrochloride.

6. The combination as claimed in claim 1 comprising 1-[(2-Bromophenyl)sulfonyl]-5-methoxy-3-[(4-methyl-1-piperazinyl)methyl]-1H-indole dimesylate monohydrate, donepezil hydrochloride and memantine hydrochloride.

7. The combination as claimed in claim 1, for treatment of cognitive disorders in a patient.

8. The combination as claimed in claim 7, wherein the cognitive disorder is selected from Alzheimer's disease, schizophrenia, Parkinson's disease, lewy body dementia, vascular dementia and frontotemporal dementia.

9. A pharmaceutical composition comprising the combination as claimed in claim 1 or claim 6, and pharmaceutically acceptable excipients or combination thereof.

10. The pharmaceutical composition as claimed in claim 9, for the treatment of cognitive disorders selected from Alzheimer's disease, schizophrenia, Parkinson's disease, lewy body dementia, vascular dementia and frontotemporal dementia.

11. The pharmaceutical composition as claimed in claim 9, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 1 mg to 300 mg.

12. The pharmaceutical composition as claimed in claim 9, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 35 mg to 200 mg.

13. The pharmaceutical composition as claimed in claim 9, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 200 mg to 300 mg.

14. The pharmaceutical composition as claimed in claim 9, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 75 mg or 150 mg.

15. The pharmaceutical composition as claimed in claim 9, wherein the donepezil or a pharmaceutically acceptable salt thereof is present in an amount of 2 mg to 30 mg.

16. The pharmaceutical composition as claimed in claim 9, wherein the memantine or a pharmaceutically acceptable salt thereof is present in an amount of 1 mg to 40 mg.

* * * * *